United States Patent [19]

Hertzberg et al.

[11] Patent Number: 5,219,530
[45] Date of Patent: Jun. 15, 1993

[54] APPARATUS FOR INITIATING PYROLYSIS USING A SHOCK WAVE

[75] Inventors: Abraham Hertzberg, Bellevue; Arthur T. Mattick, Seattle; David A. Russell, Kirkland, all of Wash.

[73] Assignee: Board of Regents of the University of Washington, Seattle, Wash.

[21] Appl. No.: 656,289

[22] Filed: Feb. 15, 1991

[51] Int. Cl.$^5$ .......................... B06B 1/00; C01G 9/12; B01D 47/02
[52] U.S. Cl. .................................. 422/127; 422/151; 422/224; 208/48 Q; 208/92; 208/128; 261/DIG. 78; 261/76
[58] Field of Search ............... 422/127, 151, 187, 224; 208/48 Q, 92, 128, 129, 130, 260; 261/76, DIG. 79; 585/476, 483, 534

[56] References Cited

U.S. PATENT DOCUMENTS

| | | | |
|---|---|---|---|
| 2,016,798 | 10/1935 | Cooke | 208/129 |
| 2,767,233 | 10/1956 | Mullen, II et al. | 208/48 Q |
| 2,790,838 | 4/1957 | Schrader | 208/48 Q |
| 3,545,886 | 12/1970 | Chalom | 261/DIG. 78 |
| 4,134,824 | 1/1979 | Kamm et al. | 208/92 |
| 4,136,015 | 7/1979 | Kamm et al. | 208/129 |
| 4,230,670 | 10/1980 | Forseth | 422/151 |
| 4,278,446 | 7/1981 | Von Rosenberg, Jr. et al. | 48/197 R |
| 4,379,679 | 4/1983 | Guile | 261/DIG. 78 |

FOREIGN PATENT DOCUMENTS

392723A 7/1983 U.S.S.R. .

Primary Examiner—Robert J. Warden
Assistant Examiner—Christopher Y. Kim
Attorney, Agent, or Firm—Christensen, O'Connor, Johnson & Kindness

[57] ABSTRACT

Apparatus for initiating pyrolysis of a feedstock by establishing a continuous, standing shock wave. Several embodiments of a shock wave reactor (10, 100, 150) are disclosed; each is connected to receive an ethane feedstock and a carrier fluid comprising superheated steam. The feedstock and the carrier fluid are pressurized so that they expand into parallel supersonic streams that mix due to turbulence within a mixing section (36) of a longitudinally extending channel (12) of the shock wave reactor. The carrier fluid heats the ethane feedstock as it mixes with it, producing a mixture that flows at supersonic velocity longitudinally down the channel. A gate valve (44) disposed downstream of the channel provides a controlled back pressure that affects the position of the shock wave and the residence time for the reaction. The shock wave rapidly heats the mixture above a pyrolysis temperature, producing a desired product by cracking the feedstock. Rapid heating of the mixture enables a residence time in the pyrolysis section of only 5 to 50 milliseconds. By varying the position of the shock wave, the residence time is controlled as required to obtain maximum yield from different feedstocks. Downstream of the pyrolysis section, the mixture is quenched, cooling and terminating the pyrolysis reaction. The relatively short residence time and the control of its duration with a resolution in the microsecond range are substantial advantages of the shock wave reactor.

12 Claims, 4 Drawing Sheets

APPARATUS FOR INITIATING PYROLYSIS USING A SHOCK WAVE

TECHNICAL FIELD

This invention generally pertains to a method and apparatus for producing a product by pyrolysis of a feedstock material, and more specifically, to the use of a shock wave to effect the pyrolysis.

BACKGROUND OF THE INVENTION

The cracking of hydrocarbons brought about by heating a feedstock material in a furnace has long been used to produce a variety of useful products. For example, ethylene, which is among the more important products in the chemical industry, can be produced by the pyrolysis of feedstocks ranging from light paraffins, such as ethane and propane, to heavier fractions such as naphtha. Typically, the lighter feedstocks produce higher ethylene yields (50–55% for ethane compared to 25–30% for naphtha); however, the cost of the feedstock is more likely to determine which is used. Since the pricing of feedstocks that may be used to produce a desired product is very volatile, it is preferable to design a pyrolysis plant to use a variety of feedstocks, enabling the most cost effective feedstock to be used in response to changing market prices.

Energy consumption is another cost factor impacting the pyrolytic production of chemical products from various feedstocks. Over the last two decades, there have been significant improvements in the efficiency of the pyrolysis process that have reduced the costs of production. In the typical or conventional pyrolysis plant, a feedstock passes through a plurality of heat exchanger tubes where it is heated externally to a pyrolysis temperature by the combustion products of fuel oil or natural gas and air. One of the more important steps taken to minimize production costs has been the reduction of the residence time for a feedstock in the heat exchanger tubes of a pyrolysis furnace. Reduction of the residence time increases the yield of the desired product while reducing the production of heavier byproducts that tend to foul the pyrolysis tube walls. Heat transfer rates can be increased by using smaller diameter, shorter tubes for the pyrolysis heat exchanger and residence times in the range of 50–100 milliseconds can thus be obtained (compared to 250–1000 milliseconds in earlier design conventional furnaces). In the production of ethylene, this provides a 5–10% increase in the yield when ethane is used as a feedstock, and a 20–30% increase in the yield for heavier feedstocks. A furnace having this range of relatively short residence times is sometimes referred to as a "millisecond furnace." Even greater increases in yield and reduction in coking are potenitially available by further shortening the residence times; however, the design of millisecond furnaces of this type does not readily permit further reduction of the residence time.

An alternative approach to heating a petroleum feedstock to a cracking or pyrolysis temperature is disclosed in U.S. Pat. No. 4,136,015. The process taught in this patent involves the injection of an atomized petroleum feedstock into a stream of hot combustion products formed by the combustion of a fuel ($H_2$ or $CH_4$) mixed with oxygen. The fuel and oxygen mix with steam in a mixing zone of the furnace and subsequently burn in a combustion zone, producing hot products of combustion that travel at a subsonic velocity into a constricting throat of the furnace. The liquid feedstock is injected into the stream of hot combustion products just upstream of the constricting throat. In the throat, the atomized liquid feedstock is mixed with and vaporized by the hot combustion products, causing an initial cracking or pyrolysis of the feedstock to occur. The mixture passes into an acceleration region where its velocity increases to a supersonic level (between Mach 1 and 2). A cross-sectional expansion of the pyrolysis zone and back pressure developed downstream produce a shock wave that increases the temperature of the mixture, effecting a final thermal cracking of the feedstock. Downstream of the shock wave, the velocity of the stream slows to a subsonic level, but the cracking process continues until the stream enters a quenching zone in which it is cooled by water injection. Finally, the quenched stream passes into a heat exchanger that recovers usable energy. This references teaches that operation of the furnace in the supersonic mode increases the production of ethylene by about 7% and substantially reduces the accumulation of burnt carbon (or coking).

In Russian Patent No. SU 392723A, a related method is disclosed for producing acetylene and ethylene via the oxidizing pyrolysis of methane. The oxidizing pyrolysis occurs in a supersonic outflow of a heated mixture of methane and oxygen from a supersonic nozzle. The reference teaches that a shock wave created in the supersonic flow raises the yield of the end products. In this method, methane and oxygen are separately preheated in heat exchangers to 800° C. and are then fed into a preliminary mixing chamber. Since the induction period is short, the mixture does not immediately ignite. Instead, the mixture cools and gathers velocity as it expands through a nozzle, achieving a supersonic speed (1500 meters/second). Upon exiting the nozzle, the supersonic stream of mixed gases impacts against a barrier, which raises the temperature sharply to the ignition temperature, causing a violent combustion of the mixture to occur. Methane molecules in a high-temperature layer of the mixture are pyrolized to ethylene and acetylene, but since the methane only resides in a high-temperature zone of the furnace for a very brief period, secondary reactions are of less importance. Water is injected into the mixture in which the methane is undergoing pyrolysis to quench the reaction.

In both of the above-referenced patents, the energy required to raise the feedstock temperatures to initiate pyrolysis is provided by combustion of feedstock or carrier fluid in an oxygen-rich environment. In the process described in U.S. Pat. No. 4,136,015 the feedstock is partially pyrolyzed by direct exposure to combustion products at temperatures as high as 2200° C., and partially pyrolyzed in the shock-heated zone downstream. As a result, uncontrolled pyrolysis of the feedstock occurs prior to heating caused by the shock wave. The temperature of the products of combustion and feedstock is thus likely to remain sufficiently high so that some coking in the furnace occurs upstream of the shock wave. In Russian Patent No. SU 392723A, the shock wave initiates combustion, again producing very high temperatures at which the feedstock is pyrolized. Accordingly, it will be apparent that merely providing a short residence time downstream of the shock wave is not sufficient; the feedstock should remain below the pyrolysis temperature until the pyrolysis reaction is initiated in a pyrolysis region. In addition, the residence time of the feedstock in the pyrolysis region of the furnace should be as brief as possible and precisely controllable to enable different feedstocks to be pyrolized, with maximum yield of the desired product.

SUMMARY OF THE INVENTION

In accordance with the present invention, an apparatus for creating a shock wave to initiate and control pyrolysis of a feedstock that is mixed with a carrier fluid includes a pyrolysis vessel having an inlet end, and downstream thereof, an outlet end. The pyrolysis vessel comprises a nozzle section disposed between the inlet end and the outlet end, which has a reduced cross-sectional area compared to that of adjacent portions of the pyrolysis vessel. A plurality of injection nozzles are disposed within the nozzle section and are connected to expand the feedstock and the carrier fluid in separate streams. Downstream of the injection nozzles is disposed a mixing section in which the carrier fluid mixes with the feedstock, and a pyrolysis section is disposed adjacent the outlet end, downstream of the mixing section.

Connected in fluid communication with the inlet end of the pyrolysis vessel is a source of carrier fluid. Means are included for heating the carrier fluid before it enters the pyrolysis vessel so that the stagnation temperature of the carrier fluid upon entry into the pyrolysis vessel is greater than that required to initiate pyrolysis of the feedstock. Means are also provided for increasing the pressure of the carrier fluid before it enters the pyrolysis vessel, so that the carrier fluid is accelerted as it passes through the nozzle section, and exits the nozzle section at a supersonic speed and at a temperature lower than that required to initiate pyrolysis of the feedstock, in a plurality of supersonic streams. Connected in fluid communication with the plurality of injection nozzles is a source of feedstock. Means for increasing the pressure of the feedstock before it enters the injection nozzles are provided, so that the feedstock exits the injection nozzles in a plurality of supersonic streams moving generally parallel to adjacent supersonic streams of carrier fluid. The supersonic streams of carrier fluid and feedstock enter the mixing section and mix turbulently in the mixing section, leaving the mixing section as a supersonic mixture. This mixture has a temperature substantially below a pyrolysis temperature that is required to initiate pyrolysis of the feedstock. The pressures of the feedstock and carrier fluid entering the pyrolysis vessel and of the mixture at the outlet end of the pyrolysis vessel create a generally continuous, stationary shock wave in the mixture. The shock wave causes an extremely rapid increase in the temperature of the mixture to a temperature exceeding the pyrolysis temperature of the feedstock, and thereby initiates conversion of the feedstock into a desired product that exits the pyrolysis section with the carrier fluid at a subsonic velocity.

The duration of the pyrolysis (defined as residence time) is a function of the shock wave position. The position of the shock wave within the pyrolysis section is controlled by adjusting the pressures of the feedstock and carrier fluid entering the pyrolysis vessel and the pressure of the mixture at the outlet end of the pyrolysis vessel. Pressure adjustment of the carrier and feedstock at the inlet end is accomplished in one preferred embodiment by varying the speed of the compression devices for these fluids. Pressure adjustment of the mixture at the outlet of the pyrolysis vessel is accomplished by throttling the flow at any point downstream of the pyrolysis vessel.

The apparatus further comprises quenching means, which are disposed downstream of the pyrolysis section, for rapidly cooling the mixture so that the pyrolysis is quenched. In one preferred form of the invention, the quenching means comprise a heat exchanber through which a cooling fluid flows in heat exchange relationship with the mixture in which the feedstock is undergoing pyrolysis. This cooling fluid thereby rapidly absorbs heat from the mixture to cool it.

In another embodiment, the quenching means comprise a turbine that cools the mixture in which the feedstock is undergoing pyrolysis by extracting work from the mixture while the mixture expands.

The apparatus can further comprise a preheat heat exchanger through which the mixture of the desired product and carrier fluid flows after it exits the pyrolysis section. The mixture thereby flows in heat exchange relationship with the carrier fluid prior to its entry into the inlet end of the pyrolysis vessel, so that the mixture preheats the carrier fluid and is cooled by it.

The apparatus can alternatively comprise means that are disposed between the mixing section and the pyrolysis section, for creating multiple weak shock waves that accumulatively rapidly heat the mixture above the pyrolysis temperature. The means for creating multiple shock waves preferably comprise a body disposed generally along the longitudinal axis of the pyrolysis vessel, such that supersonic flow of the mixture over the body develops oblique and normal shock waves relative to the longitudinal axis of the pyrolysis vessel.

Preferably, the carrier fluid entering the pyrolysis vessel comprises superheated steam. Likewise, the feedstock preferably comprises a hydrocarbon. The apparatus can also include means for preheating the feedstock, and if included, liquid feedstock can be vaporized by the means for preheating, enabling either gaseous or liquid feedstocks to be processed.

DESCRIPTION OF THE PREFERRED EMBODIMENTS

Figure 1:
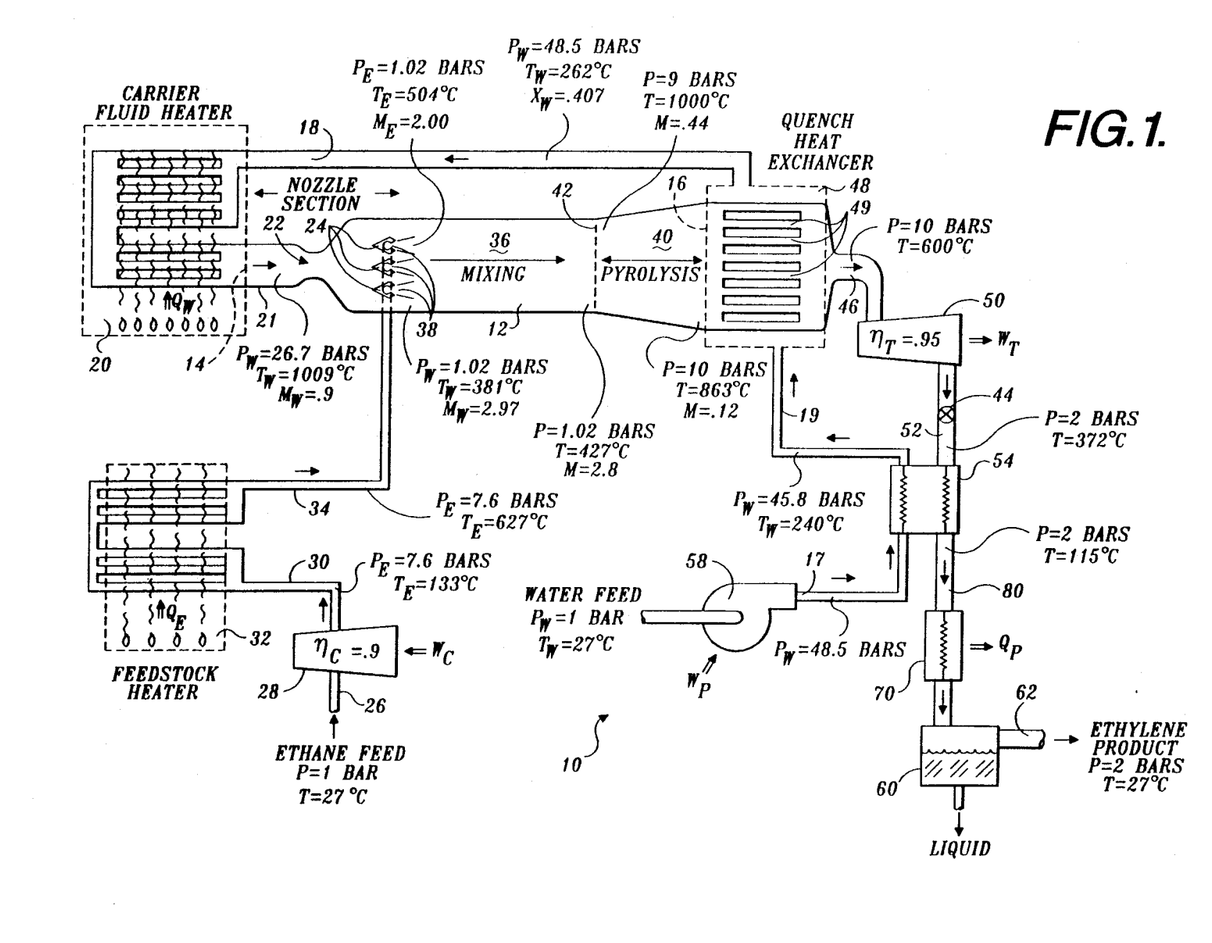
FIG. 1 is a schematic diagram illustrating a first embodiment of a shock wave reactor for initiating pyrolysis of a feedstock.

A first embodiment of a shock wave reactor 10 is shown in FIG. 1. Shock wave reactor 10 comprises a generally elongate cylindrical channel 12 that serves as a pyrolysis vessel. (This and other embodiments are described herein in respect to their predicted rather than empirical performance.) Channel 12 has an inlet end 14, and downstream thereof, an outlet end 16. A preheated carrier fluid enters inlet end 14 through a line 18. Immediately adjacent to and upstream of inlet end 14 is a heater section 20. The carrier fluid, which in the preferred embodiment comprises superheated steam, passes through heater section 20 and is heated by an externally applied source of heat. For example, fuel oil or natural gas can be externally burned with air to heat the carrier fluid as it passes through heater section 20.

As shown in FIG. 1, the carrier fluid within line 18 is a saturated mixture of water vapor and liquid at a temperature of 262° C., moving at low speed, and having a quality, $x=0.4$. However, after passing through heater section 20, the carrier fluid becomes superheated, reaching a temperaure of approximately 1009° C., and its Mach number increases to 0.9 (nearly supersonic). The purpose of accelerating the carrier fluid as it is heated is to increase the fluid's stagnation enthalpy while keeping the heater tube walls well below operational temperature limits of conventional heater tube materials.

The heated carrier fluid is conveyed in a channel 21 from heater section 20 to a nozzle section 22. This section acts as a venturi and expands the carrier fluid adiabatically to a Mach number of 3.0 and a temperature of 381° C. This relatively cool carrier fluid emerges from openings between a plurality of injection nozzles 24, at the downstream end of the nozzle section 22. Injection nozzles 24 are connected in fluid communication with a source of a feedstock. In the preferred embodiment, the feedstock comprises ethane gas. However, those of ordinary skill in the art will appreciate that other feedstocks, including various other hydrocarbons, such as propane, can be subjected to pyrolysis by shock wave reactor 10 to form a desired product. In the particular application illustrated in FIG. 1, the desired product formed by pyrolysis of ethane is ethylene.

The ethane feedstock is supplied from a source (not shown) through a line 26 to a compressor 28. Compressor 28 increases the pressure of the ethane feedstock from approximately one bar to approximately 7.6 bars. A line 30 conveys the compressed ethane feedstock to a heater 32, which raises the temperature of the feedstock from 133° C. to 627° C. through external heat addition resulting from combustion of fuel oil or natural gas and air. A line 34 conveys the preheated ethane feedstock at low Mach number to the plurality of injection nozzles 24. Preheating the feedstock provides a higher stagnation enthalpy downstream in a mixing section 36 than would be the case without feedstock preheating. This step is advantageous because it allows an increased throughput of feedstock per unit of carrier fluid.

The plurality of injection nozzles 24 accelerate the feedstock as it exits through openings 38, producing a plurality of streams, each having a Mach number of about 2.0 and a temperature of about 504° C. These feedstock streams are interleaved with and flow generally parallel to the carrier fluid streams (which are at about Mach 3.0 and 381° C.) as they exit nozzle section 22 and enter mixing section 36.

The difference between the velocities of the feedstock and carrier fluid streams in mixing section 36 leads to turbulent mixing of the feedstock and carrier fluid. As the mixing proceeds, the temperatures of the streams approach a common temperature, intermediate between the initial stream temperatures at the entrance of the mixing section. The streams of feedstock and carrier fluid fully mix in mixing section 36 and leave the section as a supersonic mixture at about Mach 2.8 and at a temperature of about 427° C.

Unlike prior art furnaces, in shock wave reactor 10, the feedstock temperature never reaches a level sufficient to initiate significant premature pyrolysis of the feedstock. Thus, it is not necessary to burn a portion of the feedstock to increase its temperature in order to initiate pyrolysis. Instead, as the carrier fluid mixes with the ethane feedstock within mixing section 36, it provides sufficient total enthalpy in the mixture to maintain the temperature of the feedstock at a level such that pyrolysis can occur as a controlled process downstream of the mixing section, even though the temperature within the mixing region is too low for pyrolysis to occur.

Downstream of mixing section 36 is disposed a pyrolysis section 40, which preferably has a gradually increasing cross-sectional area. Pyrolysis of the ethane feedstock occurs exclusively within pyrolysis section 40 due to an extremely rapid increase in the temperature of the mixture of the ethane feedstock and carrier fluid caused by the creation of a continuous, standing shock wave 42. Immediately downstream of shock wave 42, the temperature of the mixture rapidly rises to approximately 1000° C. This rapid increase in the temperature of the mixture immediately initiates pyrolysis of the ethane feedstock, converting it into ethylene, the desired product for this reaction. In addition, the pressure of the mixture downstream of shock wave 42 increases by approximately a factor of 9, and the velocity of the mixture falls to a subsonic level of about Mach 0.4. The expanding cross-sectional area of pyrolysis section 40 serves as a diffuser for the subsonic, reacting mixture downstream of the shock wave and helps to maintain a high temperature as the pyrolysis proceeds.

Shock wave 42 is created as a result of back pressure caused by the total flow restriction downstream of outlet end 16. At least part of that flow restriction may be controlled by the position of a gate valve 44, which is disposed downstream of outlet end 16 of shock wave reactor 10.

Disposed downstream of section 40 is a quench heat exchanger 48 through which the pyrolized mixture flows in a plurality of tubes 49, which are exposed to carrier fluid, so that the mixture is in heat exchange relationship with the carrier fluid. The carrier fluid flowing through quench heat exchanger 48 quenches the pyrolysis reaction and is thereby preheated prior to its entry into inlet end 14 of heater section 20. Quench heat exchanger 48 thus recovers energy from the pyrolized mixture and quickly quenches the pyrolysis reaction to minimize the production of undesired by-products.

Figure 2A:
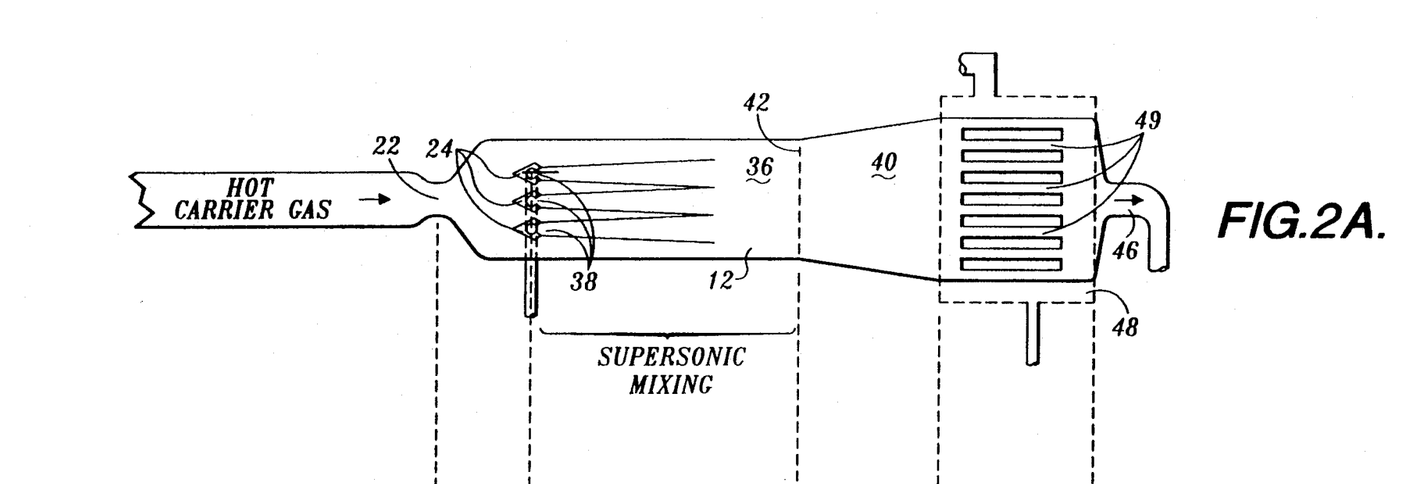
FIG. 2A schematically illustrates a portion of the shock wave reactor in which a feedstock is injected through nozzles into the supersonic flow of a carrier fluid to initiate mixing of the fluids.
Figure 2B:
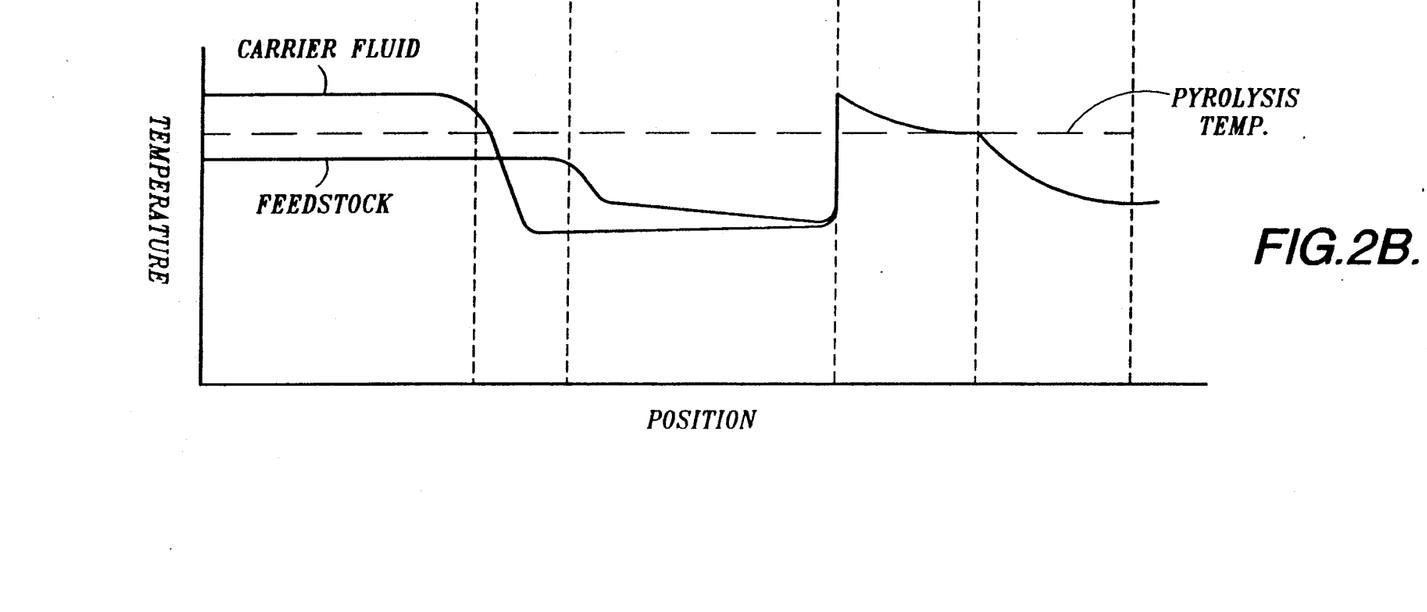
FIG. 2B is a graph of temperature versus position for both the carrier fluid and feedstock in respect to the flow of these two fluids through the shock wave reactor as shown in FIG. 2A.

FIGS. 2A and 2B illustrate the relationship of temperature and position as both the carrier fluid and feedstock flow through shock wave reactor 10. The rapid increase in temperature of the mixture at shock wave 42 is clearly evident in FIG. 2B. Although the ethane feedstock is preferably preheated prior to its injection into channel 12 through injection nozzles 24, it will be apparent that the pyrolysis reaction can also be initiated without such preheating.

Further energy recovery from the pyrolysis process is achieved by providing a turbine 50 connected to receive the products of the pyrolysis reaction conveyed through an outlet conduit 46. Expansion of the products of the pyrolysis reaction in turbine 50 further cools them, while producing useful work. The products of the pyrolysis reaction exit turbine 50 through a line 52, which passes through a heat exchanger 54. Heat transferred from the products of the pyrolysis reaction preheats water that flows through heat exchanger 54. This water is conveyed from a pump 58 to the heat exchanger in a line 17. Water is supplied from a source (not shown) at ambient conditions of temperature and pressure to the inlet of pump 58 and is pressurized to 48.5 bars by the pump. Within heat exchanger 54, the water at 48.5 bars is heated to a temperature of 240° C., and is then conveyed in a line 19 from heat exchanger 54 to quench heat exchanger 48. Heat transfer between the products of the pyrolysis reaction and the water passing through heat exchanger 54 further cools the products. The product exits heat exchanger 54 through a line 80 at a temperature of 115° C. and a pressure of 2 bars, with the water component of the product being partially condensed. The energy residing in the product issuing from heat exchanger 54 can be recovered in part as process heat, to be used in downstream separation operations. This process and further cooling to condense all of the water vapor in the product are indicated at reference numeral 70 in FIG. 1. Once cooled, the product passes to a receiver 60, wherein the liquid is extracted from the bottom, and the vapor, including the desired product, ethylene, is drawn from the top of receiver 60 and conveyed to separation and purification units (not shown) through a line 62.

One important advantage of shock wave reactor 10 is the ease with which the residence time during which pyrolysis of the ethane feedstock occurs is controlled within pyrolysis section 40. The two most significant factors affecting the residence time are the disposition of shock wave 42 and the rapidity with which the pyrolysis reaction is quenched downstream of pyrolysis section 40 by the cooling effect of the carrier feedstock flowing through quench heat exchanger 48. The use of an expanding cross-sectional area of channel 12 within the pyrolysis section 40 provides a means to anchor shock wave 42 at a desired position within shock wave reactor 10. The disposition of shock wave 42 is also controlled by the pressure of the ethane feedstock exiting injection nozzles 24 (controllable by varying the speed of compressor 28, for example) and the pressure of the carrier fluid flowing past the injection nozzles. A further factor controlling the disposition of shock wave 42 is the back pressure resulting from the variable flow restriction developed by gate valve 44.

Gate valve 44 comprises a readily controlled mechanism for adjusting the flow restriction to vary the residence time of a feedstock within pyrolysis section 40, and thus the time during which the feedstock undergoes pyrolysis. In fact, the residence time of shock wave reactor 10 can be controlled with microsecond resolution, thereby enabling it to readily accommodate different feedstock materials and variations in operating conditions. Since the rate of increase in the temperature of the feedstock immediately downstream of shock wave 42 is so great, the residence time of the feedstock within pyrolysis section 40 can be limited and controlled within the range of 5-50 milliseconds, thereby substantially reducing coking of undesired by-products on the walls of the pyrolysis section and downstream thereof. Premature pyrolysis of the feedstock is avoided, since upstream of shock wave 42, the temperature of the feedstock is always substantially less than the pyrolysis temperature. Virtually all of the pyrolysis thus takes place adiabatically downstream of shock wave 42 and the temperature of the mixture and reaction rate therefore decrease as the endothermic reaction proceeds to completion. The ratio of the carrier fluid to the ethane feedstock is sufficiently high to maintain the pyrolysis temperature, preventing a precipitous drop in temperature prior to the completion of the pyrolysis reaction.

Once the pyrolysis reaction has proceeded to the desired state (producing maximum ethylene yield in this example), rapid quenching of the mixture prevents formation of the heavier, undesired by-products. Quenching by using the mixture to produce the steam subsequently used as the carrier fluid provides efficient operation. Table 1 tabulates the expected energy inputs and outputs (as kilojoules per kilogram of ethylene produced) of the process described above. This process is believed to yield approximately 70% conversion of ethane to ethylene, the remaining by-product assumed to be hydrogen (acetylene and heavier by-products being neglected).

TABLE 1

|  |  | kJ kg-ethylene |
|---|---|---|
| Energy inputs | Ethane heat $Q_E$ | 2400 |
|  | Water heat $Q_W$ | 31820 |
| $Q = Q_E + Q_W$ | Total heat input Q | 34220 |
|  | Ethane work $W_E$ | 330 |
|  | Pump work $W_P$ | 70 |
| $W = W_E + W_P$ | Total work input W | 400 |
| Energy output: | Turbine work $W_T$ | 6210 |
|  | Process heat & cooling, $Q_p$ | 23530 |
| Energy absorbed by reaction: |  | 4800 |
| fractional conversion to ethylene: |  | 0.7 |
| kg-steam/kg-ethane: |  | 6.67 |
| kg-steam/kg-ethylene: |  | 10.20 |

Figure 3:
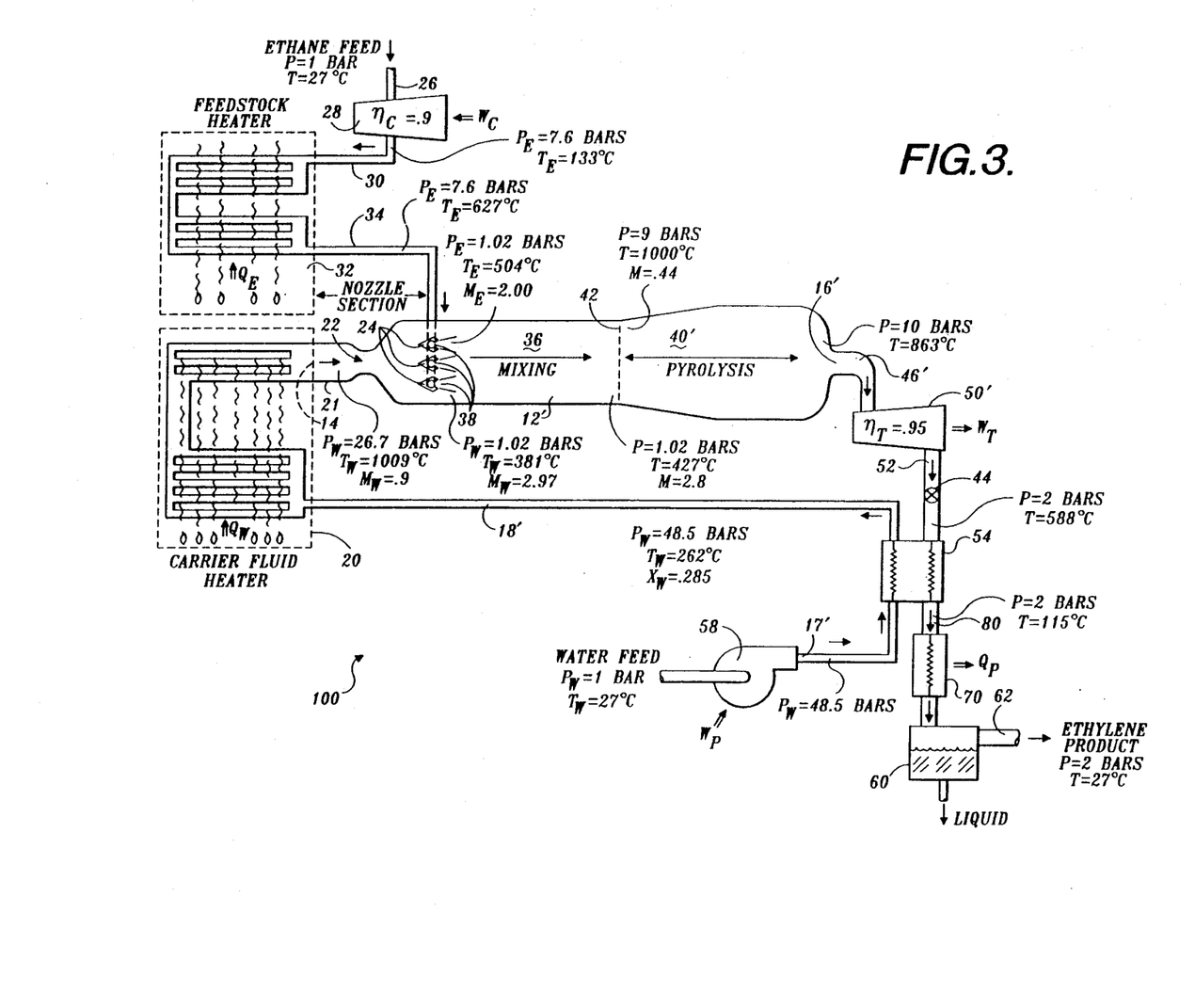
FIG. 3 is a schematic diagram illustrating a second embodiment of the shock wave reactor in which a turbine is used to cool the products of the pyrolysis reaction by expansion.

A second preferred embodiment of the shock wave reactor is shown generally in FIG. 3 at reference numeral 100. The only significant difference between shock wave reactor 10 and shock wave reactor 100 is the omission of quench heat exchanger 48 for quenching the pyrolysis reaction. Instead, in shock wave reactor 100, an outlet end 16' of a channel 12' is connected directly through an outlet conduit 46' to a turbine 50'. Accordingly, the pyrolysis reaction is quenched as the products of the reaction expand rapidly through turbine 50', producing more mechanical work than in the first embodiment. Since the carrier fluid flowing in line 18' is not preheated by heat exchange with the products of the pyrolysis reaction in shock wave reactor 100, additional heat must be applied externally to heater section 20 to raise the temperature of the carrier fluid to the necessary level required for heating the ethane feedstock prior to initiation of pyrolysis by shock wave 42. In all other respects, shock wave reactor 100 operates in much the same fashion as shock wave reactor 10. Accordingly, the same reference numerals are used for both embodiments, but with a prime notation where differences in form exist; all other reference numbers are the same.

Figure 4:
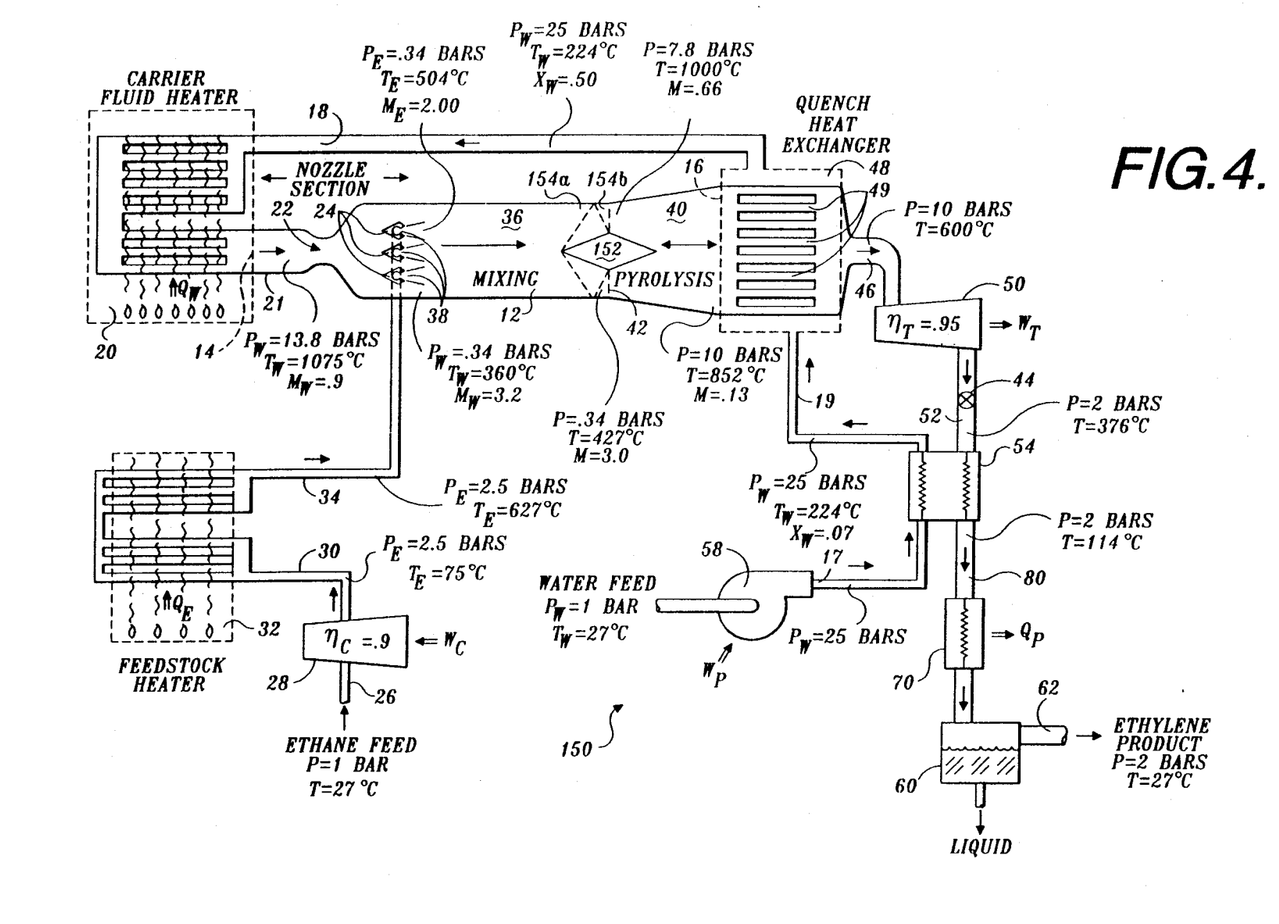
FIG. 4 is a schematic diagram illustrating a third embodiment of the shock wave reactor wherein multiple weak shock waves accumulatively initiate the pyrolysis of the feedstock fluid.

FIG. 4 shows a third embodiment of the shock wave reactor, generally at reference numeral 150. Shock wave reactor 150 is also similar in most respects to shock wave reactor 10 (and uses the same reference numbers), except that it includes a body 152 that is disposed between mixing section 36 and pyrolysis section 40. The purpose of body 152 is to assist in the formation of a plurality of weaker shock waves 154a and 154b. Shock waves 154 produce much the same rapid temperature increase in the mixture of the ethane feedstock and carrier fluid flowing through mixing section 36 into pyrolysis section 40 as the single shock wave in shock wave reactor 10. In the system of multiple shock waves, oblique shock waves 154a each contribute to an increase in temperature of the mixture, followed by a further increase due to a normal shock wave 154b. The sum of the temperature increases caused by each weak shock wave equals the net temperature increase necessary to initiate the pyrolysis reaction, enabling the ethane feedstock to undergo conversion into ethylene, the desired product. The time duration between the first of the oblique shock waves 154a and the final normal shock wave 154b experienced as the mixture flows through channel 12 is on the order of one millisecond. This time is insignificant compared with the residence time for the pyrolysis reaction, which is on the order of tens of milliseconds.

One of the advantages of using body 152 to generate a plurality of weaker shock waves 154 is the reduction in the required pressure of the mixture to which the feedstock and carrier must be compressed prior to entering the pyrolysis vessel, and the attendant reductionn in work of compression. In shock wave reactor 10, the carrier fluid has a pressure of approximately 50 bars immediately upstream of the nozzle section. In comparison, shock wave reactor 150 requires that the carrier fluid have a pressure approximately equal to only about 25 bars immediately upstream of the nozzle section. An additional advantage is that the reaction can proceed with a higher ethane-to-carrier fluid ratio, i.e., 0.2 for shock wave reactor 150 versus 0.15 for shock wave reactor 10. This higher ratio is possible because the post-shock flow speed, and therefore the stagnation enthalpy, is higher than for the single-shock case, and this extra energy is available to pyrolize a greater quantity of feedstock. However, the carrier fluid must be heated to a somewhat higher temperature upstream of injection nozzles 24 in the third embodiment, compared to its temperature in shock wave reactor 10. Table 2 tabulates the expected energy input versus energy output for shock wave reactor 150, facilitating comparison of the first and third embodiments.

TABLE 2

| | | kJ kg-ethylene |
|---|---|---|
| Energy inputs | Ethane heat $Q_E$ | 2590 |
| | Water heat $Q_W$ | 24860 |
| $Q = Q_E + Q_W$ | Total heat input Q | 27450 |
| | Ethane work $W_E$ | 140 |
| | Pump work $W_P$ | 30 |
| $W = W_E + W_P$ | Total work input W | 170 |
| Energy output: | Turbine work $W_T$ | 4870 |
| | Process heat & cooling. $Q_p$ | 17870 |
| Energy absorbed by reaction: | | 4880 |
| fractional conversion to ethylene: | | 0.7 |
| kg-steam/kg-ethane: | | 5.0 |
| kg-steam/kg-ethylene: | | 7.14 |

Those of ordinary skill in the art will appreciate that multiple bodies 152 can be mounted within channel 12 in parallel, to reduce the length of the shock system in the flow direction, and to produce multiple shock waves.

While the present invention has been disclosed in respect to several preferred embodiments and modifications thereof, it will be apparent that further modifications may be made thereto within the scope of the claims that follow. Accordingly, it is not intended that the disclosure of the preferred embodiment in any way limit the scope of this invention.

The invention in which an exclusive property or privilege is claimed is defined as follows:

1. Apparatus for creating a shock wave to initiate and control pyrolysis of a feedstock that is mixed with a carrier fluid, comprising:
   a. a pyrolysis vessel having an inlet end, and downstream thereof, an outlet end, the pyrolysis vessel including:
      i. a nozzle section disposed between the inlet end and the outlet end, the nozzle section having a reduced cross-sectional area compared to that of adjacent portions of the pyrolysis vessel;
      ii. a plurality of injection nozzles disposed within the nozzle section and connected to expand a feedstock and a carrier fluid separate streams;
      iii. a mixing section disposed downstream of the injection nozzles, in which the carrier fluid mixes with the feedstock; and
      iv. a pyrolysis section disposed adjacent the outlet end, downstream of the mixing section;
   b. means for increasing the pressure of the feedstock before the feedstock reaches the plurality of injection nozzles, so that the feedstock exits the injection nozzles and expands into the mixing section at a supersonic velocity;
   c. a carrier fluid heater in which the carrier fluid is heated upstream of the nozzle section;
   d. means for increasing the pressure of the carrier fluid before the carrier fluid enters the pyrolysis vessel, so that the carrier fluid flows through the nozzle section, expanding as it passes the plurality of injection nozzles and flows into the mixing section at a supersonic velocity, the carrier fluid turbulently mixing with the feedstock, therein producing a mixture of the feedstock and the carrier fluid that moves at a supersonic velocity through the mixing section, the mixture having a temperature substantially below that required to initiate pyrolysis of the feedstock; and
   c. a flow restriction disposed downstream of the pyrolysis vessel that creates a substantially continuous, stationary shock wave in the mixture, the shock wave causing immediate heating of mixture to a temperature above that necessary to initiate pyrolysis of the feedstock so that said pyrolysis first occurs in the pyrolysis section, thereby converting the feedstock into a desired product that exits the pyrolysis section with the carrier fluid at a subsonic velocity.

2. The apparatus of claim 1, further comprising means for varying the residence time of the feedstock in the pyrolysis section, wherein the duration of the pyrolysis is a function of the residence time of the feedstock in the pyrolysis section and is thus a function of the shock wave position.

3. The apparatus of claim 2, wherein the means for varying the residence time comprises means for varying the extent of the flow restriction.

4. The apparatus of claim 1, further comprising quenching means, disposed downstream of the pyrolysis section, for cooling the mixture so that the pyrolysis is quenched.

5. The apparatus of claim 4, wherein the quenching means comprise a heat exchanger through which a cooling fluid flows in heat exchange relationship with the mixture in which the feedstock is undergoing pyrolysis, the cooling fluid thereby absorbing heat from the mixture to cool it.

6. The apparatus of claim 4, wherein the quenching means comprise a turbine that cools the mixture in which the feedstock is undergoing pyrolysis by extracting work from the mixture while the mixture expands.

7. The apparatus of claim 1, further comprising a preheat heat exchanger through which the mixture of the desired product and carrier fluid flows after it exits the pyrolysis section, said mixture thereby flowing in heat exchange relationship with the carrier fluid prior to its entry into the pyrolysis vessel, so that the mixture preheats the carrier fluid and is cooled by it.

8. The apparatus of claim 1, further comprising means, disposed between the mixing section and the pyrolysis section, for creating multiple weak shock waves that accumulatively heat the mixture above the pyrolysis temperature.

9. The apparatus of claim 8, wherein the means for creating multiple shock waves comprise a body disposed along a longitudinal axis of the pyrolysis vessel, supersonic flow of the mixture over the body developing oblique and normal shock waves relative to the longitudinal axis of the pyrolysis vessel.

10. The apparatus of claim 1, wherein the inlet end comprises means for conveying a carrier fluid into the pyrolysis vessel, said carrier fluid comprising superheated steam.

11. The apparatus of claim 1, further comprising means for conveying a feedstock comprising a hydrocarbon to the injection nozzles.

12. The apparatus of claim 1, further comprising heater means for preheating the feedstock before it enters the pyrolysis vessel.

* * * * *